United States Patent [19]

Kwiatkowski et al.

[11] Patent Number: 5,689,006
[45] Date of Patent: *Nov. 18, 1997

[54] PROCESS FOR PRODUCING N-ALKYL-DINITROALKYLANILINES

[75] Inventors: Stefan Kwiatkowski; Krzysztof Pupek; Brenda L. Lawrence; Lowell J. Lawrence, all of Richmond, Ky.

[73] Assignee: SRM Chemical, Ltd. Co., League City, Tex.

[*] Notice: The term of this patent shall not extend beyond the expiration date of Pat. No. 5,663,441.

[21] Appl. No.: 496,774

[22] Filed: Jun. 29, 1995

[51] Int. Cl.⁶ .................... C07C 209/18; C07C 311/39
[52] U.S. Cl. ................................ 564/399; 564/87
[58] Field of Search ........................ 564/87, 399

[56] References Cited

U.S. PATENT DOCUMENTS

| | | | |
|---|---|---|---|
| 3,672,866 | 6/1972 | Damiano | 71/121 |
| 3,927,127 | 12/1975 | Damiano | 260/646 |
| 3,991,116 | 11/1976 | Damiano | 260/577 |
| 4,289,907 | 9/1981 | Chan | 564/399 |
| 4,395,572 | 7/1983 | Chan | 564/399 |

FOREIGN PATENT DOCUMENTS 0 630 883  12/1994  European Pat. Off. .

OTHER PUBLICATIONS

Olson, Walter T. et al.; "The Synthesis and Purification of Ethers"; Journal of the American Chemical Society; vol. 69, No. 10; Oct. 31, 1947; 2451–4.

Dubinin, B.M.; "Isomerizations in Organomagnesium Synthesis" Chemical Abstracts; vol. 44, No 3; Feb. 10, 1950; 1060.

*Primary Examiner*—Peter O'Sullivan
*Attorney, Agent, or Firm*—King and Schickli

[57] ABSTRACT

This invention relates to a process for producing N-alkyl-dinitroalkylaniline and particularly N-sec-butyl-4-tert-butyl-2,6-dinitroaniline by methylation of an alkylphenol followed by nitration of the resulting alkylanisole which is followed by reaction with an amine.

19 Claims, No Drawings

5,689,006

1

PROCESS FOR PRODUCING N-ALKYL-DINITROALKYLANILINES

TECHNICAL FIELD

The present invention relates generally to an improved process for the production of N-alkyl-dinitroalkylanilines in a more cost effective and efficient manner.

BACKGROUND OF THE INVENTION

N-alkyl-dinitroalkylanilines such as N-sec-butyl-4-tert-butyl-2,6-dinitroaniline [(1,1-dimethylethyl)-N-[1-methylpropyl)-2,6,dinitrobenzenamine; butralin] are known selective herbicides generally used for pre-emergence control of annual broad-leaved weeds and grasses in cotton, soybeans, rice, barley, beans, alliums, vines, ornamentals and orchards of fruit and nut trees. They are also used to control suckers of tobacco.

The synthesis of N-sec-butyl-4-tert-butyl-2,6-dinitroaniline is generally described in a number of U.S. Pat. Nos. including, for example, 3,672,866; 3,927,127 and 3,991,116 all to Damiano. The process described in U.S. Pat. Nos. 3,672,866 and 3,991,116 begins with a starting material, 4-tert-butylphenol. The 4-tert-butylphenol is subjected to nitration utilizing nitric acid in acetic acid solution to produce 2,6-dinitro-4-tert-butylphenol. The 2,6-dinitro-4-tert-butylphenol is then chlorinated to produce 2,6-dinitro-4-tert-butylchlorobenzene. This 2,6-dinitro-4-tert-butylchlorobenzene is then converted into N-sec-butyl-4-tert-butyl-2,6-dinitroaniline by amination with sec-butylamine.

While this process is effective in producing the desired product, it does suffer from a number of distinct disadvantages. First and foremost is the relatively low yield of the nitration step: only approximately 70%. Second, the process necessitates purification of the 2,6-dinitro-4-tert-butylphenol product of the nitration step by crystallization from large volumes of highly volatile and flammable hexane. This is both hazardous and time consuming. Third, is the necessity of utilizing thionyl chloride in high boiling and expensive solvents for the chlorination step. This step disadvantageously leads to the equimolar formation of toxic and environmentally hazardous gaseous by-products; hydrochloric acid and sulfur dioxide. Further, the slow fifteen hour process also necessitates further purification of the crude product from hexane thereby further elevating the costs of production. Fourth, the amination step requires seven hours and the use of excessive amounts of sec-butylamine while unfortunately being accompanied by the formation of equimolar quantities of sec-butylamine hydrochloride as a by-product.

The process described in U.S. Pat. No. 3,927,127 begins with a starting material, 4-tert-butylchlorobenzene. The 4-tert-butylchlorobenzene is subjected to nitration utilizing a mixture of nitric and sulfuric acids to produce 2,6-dinitro-4-tert-butylchlorobenzene. The 2,6-dinitro-4-tert-butylchlorobenzene is then converted to N-sec-butyl-4-tert-butyl-2,6-dinitroaniline by amination with sec-butylamine. While the process is effective in producing the desired product, it does suffer from a number of distinct shortcomings. First and foremost, it is necessary to use a highly concentrated nitric and sulfuric acid mixture at elevated temperatures for a prolonged time to complete the nitration step of the synthesis. This unfortunately involves a substantial risk of explosion. Second, it is necessary to use an excess of sec-butylamine because of the equimolar formation of a sec-butylamine hydrochloride as a by-product in the third stage of the process. This, unfortunately, necessitates the application of a high boiling point solvent (e.g. xylene) to allow filtration separation of the by-product thereby producing a number of additional safety hazards and environmental concerns.

An alternative synthesis for N-sec-butyl-4-tert-butyl-2,6-dinitroaniline is set forth in U.S. Pat. Nos. 4,289,907 and 4,395,572 to Chan. The starting material in this synthesis is a nitrophenol such as 2,6-dinitro-4-tert-butylphenol. The nitrophenol is methylated by reaction with methyl iodide/potassium carbonate to produce 4-tert-butyl-2,6-dinitroanisole. The 4-tert-butyl-2,6-dinitroanisole is then reacted with sec-butylamine to produce N-sec-butyl-4-tert-butyl-2,6-dinitroaniline. While effective in producing the desired product, this process also suffers from a number of distinct disadvantages.

First, the process involves the use of methyl iodide. This material is expensive, volatile, carcinogenic and poisonous. The resulting health and environmental concerns require the establishment of special handling procedures.

Second, the resulting yield of the process is only approximately 71%. Third, the product is accompanied by the formation of bulk amounts of gaseous, liquid and solid waste including the carcinogenic methyl iodide starting material. Fourth, the process involves the use of excess amounts of potassium carbonate and highly flammable and volatile acetone as a solvent. This adds to the expenses and handling concerns of the process.

From the above description it should be appreciated that a need exists for an improved process for producing N-alkyl-dinitroalkylanilines in a more economical and environmentally safer manner.

SUMMARY OF THE INVENTION

Accordingly, it is a primary object of the present invention to provide a process for the production of N-alkyl-dinitroalkylanilines including, for example, N-sec-butyl-4-tert-butyl-2,6-dinitroaniline overcoming the above-identified limitations and disadvantages of the prior art.

Another object of the invention is to provide a process for the production of N-alkyl-dinitroalkylaniline from readily available and relatively inexpensive starting materials and relatively safe and inexpensive reagents whereby the environmentally safe and economical production of N-alkyl-dinitroalkylaniline results.

Other objects and advantages of the present invention will become apparent as the description hereof proceeds.

In satisfaction of the foregoing objects and advantages there is provided by this invention a process for producing N-alkyl-dinitroalkylanilines. The process generally comprises the reacting of an alkylphenol with a methylating agent such as dialkyl sulfate to produce an alkylanisole intermediate. The alkylanisole intermediate is then reacted with a nitrating agent such as nitric acid to produce a dinitro-substituted alkylanisole. The dinitro-substituted alkylanisole is then reacted with an amine to produce the desired N-alkyl-dinitroalkylaniline product.

More specifically, the process for producing N-sec-butyl-4-tert-butyl-2,6-dinitroaniline comprises reacting 4-tert-butylphenol with dimethyl sulfate to produce 4-tert-butylanisole. The 4-tert-butylanisole is then reacted with nitrating agent to produce 2,6-dinitro-4-tert-butylanisole. The 2,6-dinitro-4-tert-butylanisole is then reacted with sec-butylamine to produce N-sec-butyl-4-tert-butyl-2,6-dinitroaniline.

DETAILED DESCRIPTION OF THE INVENTION

As indicated above, the present invention relates to a process for producing N-alkyl-dinitroalkylanilines of a type known to be useful as selective herbicides used for pre-emergence control of annual broad-leaved weeds and grasses in, for example, cotton, soybeans, rice, barley, beans, alliums, vines, ornamentals and orchards of fruit and nut trees as well as to control suckers of tobacco. Active compounds that may be produced utilizing the present process include, but are not limited to, butralin and pendimethalin, oryzalin and nitralin. Advantageously, the present process allows the efficient and inexpensive production of the N-alkyl-dinitroalkylanilines in an environmentally safe manner.

The process may be generally described as comprising the steps of: (1) reacting an alkylphenol with a methylating agent to produce an alkylanisole intermediate; (2) reacting the alkyl anisole intermediate with a nitrating agent to produce a dinitro-substituted alkylanisole; and (3) reacting the dinitro-substituted alkylanisole with an amine to produce N-alkyl-dinitroalkylaniline.

More specifically describing the invention, the first step of the synthesis includes the preparing of an aqueous suspension of alkylphenol followed by the adding of sodium hydroxide and a dialkyl sulfate such as dimethyl sulfate into the aqueous suspension at a temperature of between substantially 5°–55° C. while maintaining a pH between substantially pH 7.5–9.5. This is followed by the collecting of the alkylanisole intermediate which is formed as an upper layer on the two layer system that is produced.

The second step of the synthesis may be more specifically described as including the mixing of one part alkylanisole intermediate with between substantially 0–9 parts by volume organic solvent selected from a group consisting of acetic anhydride, acetic acid and mixtures thereof. This is followed by the cooling of the reaction mixture of the alkylanisole intermediate and organic solvent to a temperature below 0° C. Next is the adding of nitric acid with a density higher than substantially 1.4 g/ml to the cooled reaction mixture to produce a dinitro-substituted alkylanisole. The reaction mixture is then added to water at a temperature below substantially 5° C. Preferably, the water has a volume at least 5 times greater than the reaction mixture. This is then followed by the filtering and washing of the nitro-substituted alkylanisole intermediate with water until reaching a pH of substantially pH of 5.5–7.0.

The third step of the synthesis may be more specifically described as including the mixing of substantially two parts by weight dinitro-substituted alkylanisole intermediate with substantially one part of amine (e.g. sec-butylamine) at a temperature of above substantially 45° C. for at least one hour. This is followed by diluting the reaction mixture with one volume part of methanol and filtration of the product.

Stated another way, the process may be broadly described as including the steps of reacting an alkylphenol of a formula:

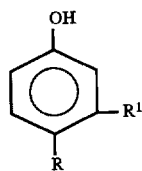

wherein: R=an alkyl group with 1–10 carbon atoms, CH$_3$SO$_2$— or H$_2$NSO$_2$—
R$^1$=—H or —CH$_3$
with a methylating agent selected from a group consisting of dialkylsulfates to produce a first reaction intermediate. This first reaction may be described as follows:

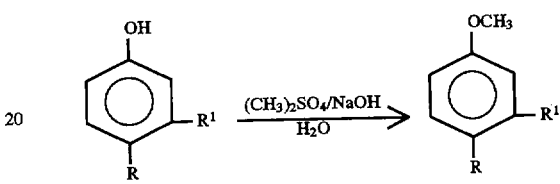

wherein R=an alkyl group with 1–10 carbon atoms, CH$_3$SO$_2$— or H$_2$NSO$_2$—
R$^1$=—H or —CH$_3$ Next is the reacting of the first reaction intermediate with a nitrating agent selected from but not limited to a group consisting of nitric acid, acetyl nitrate and a mixture of nitric acid and acetic anhydride to produce a second reaction intermediate.

This second reaction may be described as follows:

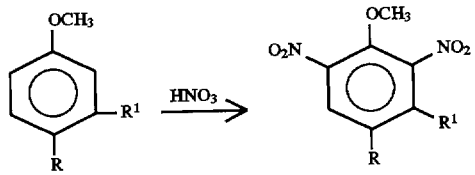

wherein R=an alkyl group with 1–10 carbon atoms, CH$_3$SO$_2$— or H$_2$NSO$_2$—
R$^1$=—H or —CH$_3$ This is followed by the reacting of the second reaction intermediate with an amine selected from a group including sec-butylamine and 1-ethylpropylamine to produce N-alkyl-dinitroalkyl-anilines. This third reaction may be described as follows:

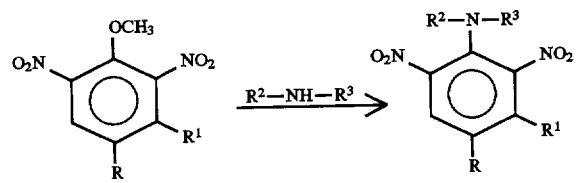

wherein R=an alkyl group with 1–10 carbon atoms, CH$_3$SO$_2$— or H$_2$NSO$_2$—;
R$^1$=—H or —CH$_3$;
R$^2$=H—; n—C$_3$H$_7$—;
R$^3$=n—C$_3$H$_7$—, sec-butyl—, 1-ethylpropyl—.

The detailed procedural description of these broadly described reaction steps is exactly as previously described.

The process of the present invention for producing N-alkyl-dinitroalkylanilines may also utilize alkylanisole starting materials. In this situation it is a two step reaction: that is the reacting of an alkylanisole with a nitrating agent selected from a group consisting of nitric acid, acetyl nitrate and a mixture of nitric acid and acetic anhydride to produce a reaction intermediate and the reacting of the reaction intermediate with an amine selected from a group consisting of sec-butylamine and 1-ethylpropylamine, to produce the N-alkyl-dinitroalkylaniline.

In accordance with a more specific aspect of the present invention, a process is provided for producing N-sec-butyl-4-tert-butyl-2,6-dinitroaniline. The process may be broadly described as: (1) reacting 4-tert-butylphenol with dimethyl sulfate to produce 4-tert-butylanisole (a methylation reaction); (2) reacting the 4-tert-butylanisole with nitric acid to produce 2,6-dinitro-4-tert-butylanisole (a nitration reaction); and (3) reacting the 2,6-dinitro-4-tert-butylanisole with sec-butylamine to produce N-sec-butyl-4-tert-butyl-2,6-dinitroaniline (an amination reaction).

More specifically describing the process, initially there is the preparing of an aqueous suspension of 4-tert-butylphenol. This is followed by the adding of sodium hydroxide and dimethyl sulfate into the aqueous suspension at a temperature of between substantially 5°–55° C. while maintaining a pH between substantially pH 7.5–9.5. This is followed by the collecting of the 4-tert-butylanisole as an upper layer of the two layer system that is produced. The 4-tert-butylanisole may be purified, if desired, by any manner known in the art including distillation.

Next is the mixing of one part 4-tert-butylanisole with between substantially 0–9 parts (by volume) organic solvent selected from a group consisting of acetic anhydride, acetic acid and mixtures thereof. Next is the cooling of the reaction mixture of 4-tert-butylamine and organic solvent to a temperature below 0° C. This is followed by the adding of nitric acid with a density higher than substantially 1.4 g/ml, pure or dissolved in 1–10 parts of acetic acid to the cooled mixture to produce 2,6-dinitro-4-tert-butylanisole. This is followed by the adding of the entire 2,6-dinitro-4-tert-butylanisole reaction mixture to water at a temperature of below substantially 5° C. Preferably, the water has a volume at least 5 times and more preferably 10 times greater than the volume of the 2,6-dinitro-4-tert-butylanisole reaction mixture. 2,6-dinitro-4-tert-butylanisole is then recovered by filtering and washing with water until reaching a pH of substantially pH 5.5–7.0. The 2,6-dinitro-4-tert-butylanisole may be purified, if desired, by washing with cold methyl alcohol.

Two parts of the recovered 2,6-dinitro-4-tert-butylanisole is then mixed with substantially one part sec-butylamine at a temperature of above substantially 45° C. for at least one hour and more preferably four hours. This is followed by the diluting of the reaction mixture with one volume part of methyl alcohol and filtration to collect the N-sec-butyl-4-tert-butyl-2,6-dinitroaniline product.

In accordance with another aspect of the present invention, a two step process for producing N-sec-butyl-4-tert-butyl-2,6-dinitroaniline comprises the steps of reacting 4-tert-butylanisole with a nitrating agent selected from a group consisting of nitric acid, acetyl nitrate and a mixture of nitric acid and acetic anhydride to produce a reaction intermediate and reacting the reaction intermediate with sec-butylamine to produce N-sec-butyl-4-tert-butyl-2,6-dinitroaniline.

Advantageously, the process of the present invention produces high yields of the product being a minimum of 97% pure if high purity reagents are utilized. The following synthesis and examples are presented to further illustrate the invention, but it is not to be considered as limited thereto.

EXAMPLE 1

Reaction 1

Methylation

To a reactor equipped with a mechanical stirrer, two dropping funnels, a thermometer and a pH measuring electrode, were added 7.5 grams (50 mmols) of 99% pure 4-tert-butylphenol (available from ALDRICH of Milwaukee, Wis.) and 30 ml of water and this mixture was warmed up to 35° C. and stirred vigorously. Next a solution of 2.2 grams (55 mmols) of sodium hydroxide, 97.8% pure (available from ALDRICH of Milwaukee, Wis.) in 7.8 ml of water and 9.5 g, 7.1 ml (75 mmols) of a 99% pure dimethyl sulfate (available from ALDRICH of Milwaukee, Wis.) were dropped into the reactor simultaneously with vigorous stirring of the reaction mixture. During this process, the temperature was maintained between 35°–37° C. and the pH of the mixture was maintained between 9.0–9.5. The addition was completed in 45 minutes.

After that time, the reaction mixture was stirred for an additional 30 minutes and then cooled to ambient temperature without stirring. The upper oily layer was then collected in an amount of 8.04 g (98% yield) and used in the nitration step of the process without further purification.

Reaction 2

Nitration

In a reactor equipped with a mechanical stirrer, a thermometer and a dropping funnel was added the intermediate product from the methylation step, 8.04 g of 4-tert-butylanisole, and 21.15 g (19.5 ml, 207 mmols) of 99% pure acetic anhydride (as available from ALDRICH of Milwaukee, Wis.). The resulting solution was cooled to –15° C. by immersing the reactor in a brine-$CO_2$ cooling bath. Vigorous stirring was then applied and a solution of 6.8 ml (146 mmols) of 90% nitric acid (1.51 g/cm$^3$) in 7.8 ml of acetic acid was dropped into the reactor within 40 minutes while maintaining the temperature of the reacting mixture below –12° C. After that time the reaction mixture was stirred at –12° C. for 1.5 hours and the contents of the reactor were poured into 220 ml of stirred icy-water. The white-creamy precipitate that was formed was filtered off and washed with water until the pH of the filtrate reached 5.5. The product was dried off while keeping it under suction on the filter. That product weighed 12.2 g and contained 11.7 g of 98.2.% pure 4-tert-butyl-2,6-dinitroanisole and 0.5 g of water.

Reaction 3

Amination

The product of the nitration step, 12.2 g of 4-tert-butyl-2,6-dinitroanisole, was added to a reactor equipped with a stirrer, a thermometer, and a reflux condenser along with 10.5 ml (7.8 g, 107 mmols) of sec-butylamine, 99% pure (as available from ALDRICH of Milwaukee, Wis.). The mixture was stirred slowly as the sec-butyl amine was added to the 4-tert-butyl-2,6-dinitroanisole. The temperature of the reaction mixture was then increased up to 50° C. and maintained for 4 hours. After that time, 15 ml of methyl alcohol was added into the reaction mixture. Then the mixture was cooled in an ice bath and the product was filtered off as an intense orange crystalline mass that weighed 13.46 g and had a melting point between 59°–61° C. The product, identified as N-sec-butyl-4-tert-butyl-2,6-dinitroaniline was 98.1% pure by liquid chromatography and, therefore, the process provided a total yield of 91.2%.

EXAMPLE 2

Reaction 1

Methylation

The process was carried out as described in Example 1 with the exception that only 96% pure 4-tert-butylphenol was used as a starting material and the crude product was purified by a vacuum distillation. The fraction distilling at a 121° C. at 25 mmHg was collected in an amount of 7.46 g including 98.6% 4-tert-butylanisole, 1.3% 4-tert-butylphenol and 0.1% of 3 unidentified components.

Reaction 2

Nitration

The process was carried out in the same manner as the nitration step set forth in Example 1 with the exception that 98.6% pure 4-tert-butylanisole (8.21 g, 50 mmols) was used as a starting material and the final product was additionally washed on the filter with three 6 ml portions each of cold methyl alcohol. That resulted in light yellow crystals that were dried under vacuum. The product weighed 11.2 g (88% yield) and contained 98.5% of 4-tert-butyl-2,6-dinitroanisole, 1.2% of 2,4-dinitroanisole and 0.3% of 3 unidentified components. The melting point was 97°–98° C.

Reaction 3

Amination

The process was carried out in the same manner as described in Example 1 above with the exception that 98.5% of pure 4-tert-butyl-2,6-dinitroanisole (12.22 g, 50 mmols) was used as a starting material. The amount of the product was 14.62 g (99.0% yield) and purity by liquid chromatography of the N-sec-butyl-4-tert-butyl-2,6-dinitroaniline was 99.4%. The mixture also included N-sec-butyl-2,4-dinitroaniline in the amount of 0.2%. 0.4% of the mixture was made up of 4 non-identified components. The product had a melting point of 59.5°–61° C.

In summary, numerous benefits have been described which result from employing the concepts of the present invention. A more environmentally sound and economical process for the production of N-alkyl-dinitroalkylaniline has been described. In this description, reference has been made to certain preferred steps in the process. However, as obvious modifications or variations thereof will become apparent to those skilled in the art, the invention is not to be considered as limited thereto.

We claim:

1. A process for producing N-sec-butyl-4-tert-butyl-2,6-dinitroaniline, comprising:

reacting 4-tert-butylphenol with dimethyl sulfate to produce 4-tert-butylanisole;

reacting 4-tert-butylanisole with nitric acid to produce 4-tert-butyl-2,6-dinitroanisole; and reacting 4-tert-butyl-2,6-dinitroanisole with sec-butylamine to produce N-sec-butyl-4-tert-butyl-2,6-dinitroaniline.

2. The process set forth in claim 1, wherein said reacting of 4-tert-butylphenol with dimethyl sulfate includes:

(a) preparing an aqueous suspension of 4-tert-butylphenol;

(b) adding metal hydroxide and dimethyl sulfate into said aqueous suspension; and (c) collecting 4-tert-butylanisole as an upper layer of a resulting post reaction two-layer system.

3. The process set forth in claim 1, wherein said reacting of 4-tert-butylanisole with nitric acid includes:

(a) mixing 4-tert-butylanisole with organic solvent selected from a group consisting of acetic anhydride, acetic acid and mixtures thereof;

(b) cooling the reaction mixture of 4-tert-butylanisole and organic solvent;

(c) adding nitric acid to the cooled reaction mixture to produce 4-tert-butyl-2,6-dinitroanisole;

(d) adding the 4-tert-butyl-2,6-dinitroanisole containing reaction mixture to water; and (e) filtering and washing said 4-tert-butyl-2,6-dinitroanisole with water.

4. The process set forth in claim 1, wherein said reacting of 4-tert-butyl-2,6-dinitroanisole with sec-butylamine includes:

(a) mixing about two parts by weight of 4-tert-butyl-2,6-dinitroanisole with about one part by volume sec-butylamine; and (b) filtering off N-sec-butyl-4-tert-butyl-2,6-dinitroaniline.

5. A process for producing N-sec-butyl-4-tert-butyl-2,6-dinitroaniline, comprising:

reacting 4-tert-butylphenol with a halide free methylating agent to produce a first reaction intermediate;

reacting said first reaction intermediate with a nitrating agent to produce a second reaction intermediate; and reacting said second reaction intermediate with sec-butylamine to produce N-sec-butyl-4-tert-butyl-2,6-dinitroaniline.

6. A process for producing N-sec-butyl-4-tert-butyl-2,6-dinitroaniline, comprising:

reacting 4-tert-butylanisole with a nitrating agent to produce a reaction intermediate; and reacting said reaction intermediate with sec-butylamine to produce N-sec-butyl-4-tert-butyl-2,6-dinitroaniline.

7. A process for producing an N-alkyl-dinitroalkylaniline comprising:

reacting an alkylphenol with a methylating agent to produce an alkylantsole intermediate;

reacting the alkylanisole intermediate with a nitrating agent to produce a dinitro-substituted alkylanisole intermediate;

reacting the dinitro-substituted alkylanisole intermediate with an amine to produce an N-alkyl-dinitroalkylaniline.

8. The process set forth in claim 7, wherein said reacting of alkylphenol with a methylating agent includes:

(a) preparing an aqueous suspension of alkylphenol;

(b) adding metal hydroxide and a dialkyl sulfate into said aqueous suspension; and (c) collecting alkylanisole as an upper layer of a resulting two-layer reaction system.

9. The process set forth in claim 7, wherein said reacting of alkylanisole intermediate with the nitrating agent includes:

(a) mixing alkylanisole with organic solvent selected from a group consisting of acetic anhydride, acetic acid and mixtures thereof;

(b) cooling the reaction mixture of alkylanisole intermediate and organic solvent;

(c) adding nitric acid to the cooled reaction mixture to produce dinitro-substituted alkylanisole intermediate;

(d) adding the dinitro-substituted alkylanisole intermediate reaction mixture to water; and (e) filtering and washing said dinitro-substituted alkylanisole intermediate with water.

10. The process set forth in claim 7, wherein said reacting of dinitro-substituted alkylanisole intermediate with amine includes:

(a) mixing about two parts of dinitro-substituted alkylanisole intermediate with about one part amine; and (b) cooling that mixture and filtering off the N-alkyl-dinitroalkylaniline.

11. A process for producing N-alkyl-dinitroalkylaniline, comprising:

reacting an alkylphenol of a formula:

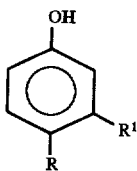

wherein R=an alkyl group with one to ten carbon atoms, $CF_3$, $CH_3SO_2$— or $H_2NSO_2$—;
$R^1$=—H or —$CH_3$;

with a halide-free methylating agent to produce a first reaction intermediate;

reacting said first reaction intermediate with a nitrating agent to produce a second reaction intermediate;

reacting said second reaction intermediate with an amine selected from a group including sec-butylamine and 1-ethylpropylamine to produce N-alkyl-dinitroalkylaniline.

12. The process set forth in claim 11, wherein said reacting of alkylphenol with methylating agent includes:

(a) preparing an aqueous suspension of alkylphenol;

(b) adding a metal hydroxide and a dialkyl sulfate or mixture thereof into said aqueous suspension; and (c) collecting the first reaction intermediate as an upper layer of a resulting two layer system.

13. The process set forth in claim 11, wherein said reacting of the first reaction intermediate with nitrating agent includes:

(a) mixing the first reaction intermediate with an organic solvent selected from a group consisting of acetic anhydride, acetic acid and mixtures thereof;

(b) cooling the reaction mixture of the first reaction intermediate and organic solvent;

(c) adding nitrating agent to the cooled reaction mixture to produce the second reaction intermediate;

(d) adding the second reaction intermediate reaction mixture to water; and (e) filtering and washing said second reaction intermediate with water.

14. The process set forth in claim 11, wherein said reacting of the second reaction intermediate with amine includes:

(a) mixing about two parts by weight of second reaction intermediate with about one part amine (b) cooling that mixture and filtering off the N-alkyl-dinitroalkylaniline.

15. A process for producing N-alkyl-dinitroalkylaniline, comprising:

reacting an alkyl anisole with a nitrating agent selected from a group consisting of nitric acid, acetyl nitrate, a mixture of nitric acid and acetic anhydride and mixtures thereof to produce a reaction intermediate; and reacting said reaction intermediate with an amine selected from a group consisting of sec-butylamine and 1-ethylpropylamine to produce N-alkyl-dinitroalkylaniline.

16. A process for producing N-sec-butyl-4-tert-butyl-2,6-dinitroaniline, comprising:

reacting 4-tert-butylphenol with dimethyl sulfate to produce 4-tert-butylanisole;

reacting 4-tert-butylanisole with nitric acid and acetic anhydride to produce 4-tert-butyl-2,6-dinitroanisole;

reacting 4-tert-butyl-2,6-dinitroanisole with sec-butylamine to produce N-sec-butyl-4-tert-butyl-2,6-dinitroaniline; and reacting the acetic acid by-product produced during the process with ketene to produce acetic anhydride for use in subsequent processing.

17. The process set forth in claim 16, wherein said reacting of 4-tert-butylphenol with dimethyl sulfate includes:

(a) preparing an aqueous suspension of 4-tert-butylphenol;

(b) adding metal hydroxide and dimethyl sulfate into said aqueous suspension; and (c) collecting 4-tert-butylanisole as an upper layer of a resulting post reaction two-layer system.

18. The process set forth in claim 17, wherein said reacting of 4-tert-butylanisole with nitric acid and acetic anhydride includes:

(a) mixing about one part 4-tert-butylanisole with about 0–9 parts by volume of organic solvent selected from a group consisting of acetic anhydride, acetic acid and mixtures thereof;

(b) cooling the reaction mixture of 4-tert-butylanisole and organic solvent;

(c) adding nitric acid to the cooled reaction mixture to produce 4-tert-butyl-2,6-dinitroanisole;

(d) filtering off the precipitated 4-tert-butyl-2,6-dinitroanisole and pouring the filtrate into water at a temperature of below about 5° C. to precipitate the rest of the 4-tert-butyl-2,6-dinitroanisole; and (e) filtering and washing said 4-tert-butyl-2,6-dinitroanisole precipitates with water.

19. The process set forth in claim 16, wherein said reacting of 4-tert-butyl-2,6-dinitroanisole with sec-butylamine includes:

(a) mixing about two parts by weight of 4-tert-butyl-2,6-dinitroanisole with about one part sec-butylamine and one part of methyl alcohol; and (b) stripping off the volatile by-products to afford N-sec-butyl-4-tert-butyl-2,6-dinitroaniline.

* * * * *

UNITED STATES PATENT AND TRADEMARK OFFICE
CERTIFICATE OF CORRECTION

PATENT NO : 5,689,006
DATED : November 18, 1997
INVENTOR(S) : Stefan NMI Kwiatkowski et al.

It is certified that error appears in the above-identified patent and that said Letters Patent is hereby corrected as shown below:

Col. 8, line 46
 replace "alkylantsole"
 with --alkylanisole--.

Signed and Sealed this

Twenty-ninth Day of September, 1998

Attest:

BRUCE LEHMAN

Attesting Officer

Commissioner of Patents and Trademarks